(12) United States Patent
Philipps

(10) Patent No.: US 9,968,697 B1
(45) Date of Patent: May 15, 2018

(54) UV SANITIZING CABINET FOR SANITIZING GARMENTS AND THE LIKE

(71) Applicant: Eric Philipps, Miami Shores, FL (US)

(72) Inventor: Eric Philipps, Miami Shores, FL (US)

( * ) Notice: Subject to any disclaimer, the term of this patent is extended or adjusted under 35 U.S.C. 154(b) by 0 days. days.

(21) Appl. No.: 15/284,828

(22) Filed: Oct. 4, 2016

(51) Int. Cl.
*A61L 2/10* (2006.01)
*A61L 2/24* (2006.01)

(52) U.S. Cl.
CPC .. *A61L 2/10* (2013.01); *A61L 2/24* (2013.01)

(58) Field of Classification Search
CPC ...................................... A61L 2/10; A61L 2/24
See application file for complete search history.

(56) References Cited

U.S. PATENT DOCUMENTS

| D435,363 | S | 12/2000 | Felsenthal | |
|---|---|---|---|---|
| 6,361,130 | B1 * | 3/2002 | Kardy | A47B 81/00 211/85.2 |
| 6,576,190 | B1 | 6/2003 | Park | |
| 7,507,369 | B2 | 3/2009 | Lu | |
| 9,107,973 | B1 | 8/2015 | Robinson | |
| 9,114,183 | B2 | 8/2015 | Campagna | |
| 9,162,001 | B2 | 10/2015 | Sunkara | |
| 2004/0016887 | A1 * | 1/2004 | Fink | A23L 3/28 250/435 |
| 2005/0023483 | A1 * | 2/2005 | Fenc | A61L 2/10 250/455.11 |
| 2012/0153783 | A1 * | 6/2012 | Shoenfeld | A61L 2/10 312/209 |
| 2013/0199581 | A1 | 8/2013 | Christopherson | |
| 2013/0214174 | A1 * | 8/2013 | Domenig | G02B 5/0278 250/455.11 |
| 2014/0301893 | A1 * | 10/2014 | Stroup | A61L 2/10 422/24 |
| 2014/0360213 | A1 * | 12/2014 | Son | F25D 29/00 62/177 |
| 2015/0118107 | A1 * | 4/2015 | Sunkara | A61L 2/24 422/24 |

FOREIGN PATENT DOCUMENTS

WO        2014205366 A     12/2014

* cited by examiner

*Primary Examiner* — Jason McCormack
*Assistant Examiner* — Sean Luck

(57) ABSTRACT

The UV sanitizing device is a wheeled cart that is adapted for use in sanitizing the garments and personal equipment used by health care professionals. The UV sanitizing device uses ultraviolet radiation to sanitize objects contained within the cabinet. The interior surfaces of the cabinet supports a plurality of UV chambers that generate the UV radiation required for use in sanitizing the contents of the cabinet. The cabinet is further organized into two chambers such that shoes can be sanitized separately from the other articles being sanitized. The UV sanitizing device comprises a cabinet, a plurality of UV chambers, a plurality of wheels, a closure, a first container, and a second container.

3 Claims, 7 Drawing Sheets

UV SANITIZING CABINET FOR SANITIZING GARMENTS AND THE LIKE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical or veterinary science including hygiene, more specifically, an apparatus for disinfecting or sanitizing objects other than foodstuffs and contact lenses using ultraviolet radiation.

SUMMARY OF INVENTION

The UV sanitizing device is a wheeled cart that is adapted for use in sanitizing the garments and personal equipment used by health care professionals. The UV sanitizing device uses ultraviolet radiation to sanitize objects contained within the cabinet. The interior surfaces of the cabinet supports a plurality of UV chambers that generate the UV radiation required for use in sanitizing the contents of the cabinet. The cabinet is further organized into two chambers such that shoes can be sanitized separately from the other articles being sanitized.

These together with additional objects, features and advantages of the UV sanitizing device will be readily apparent to those of ordinary skill in the art upon reading the following detailed description of the presently preferred, but nonetheless illustrative, embodiments when taken in conjunction with the accompanying drawings.

In this respect, before explaining the current embodiments of the UV sanitizing device in detail, it is to be understood that the UV sanitizing device is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the UV sanitizing device.

It is therefore important that the claims be regarded as including such equivalent construction insofar as they do not depart from the spirit and scope of the UV sanitizing device. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
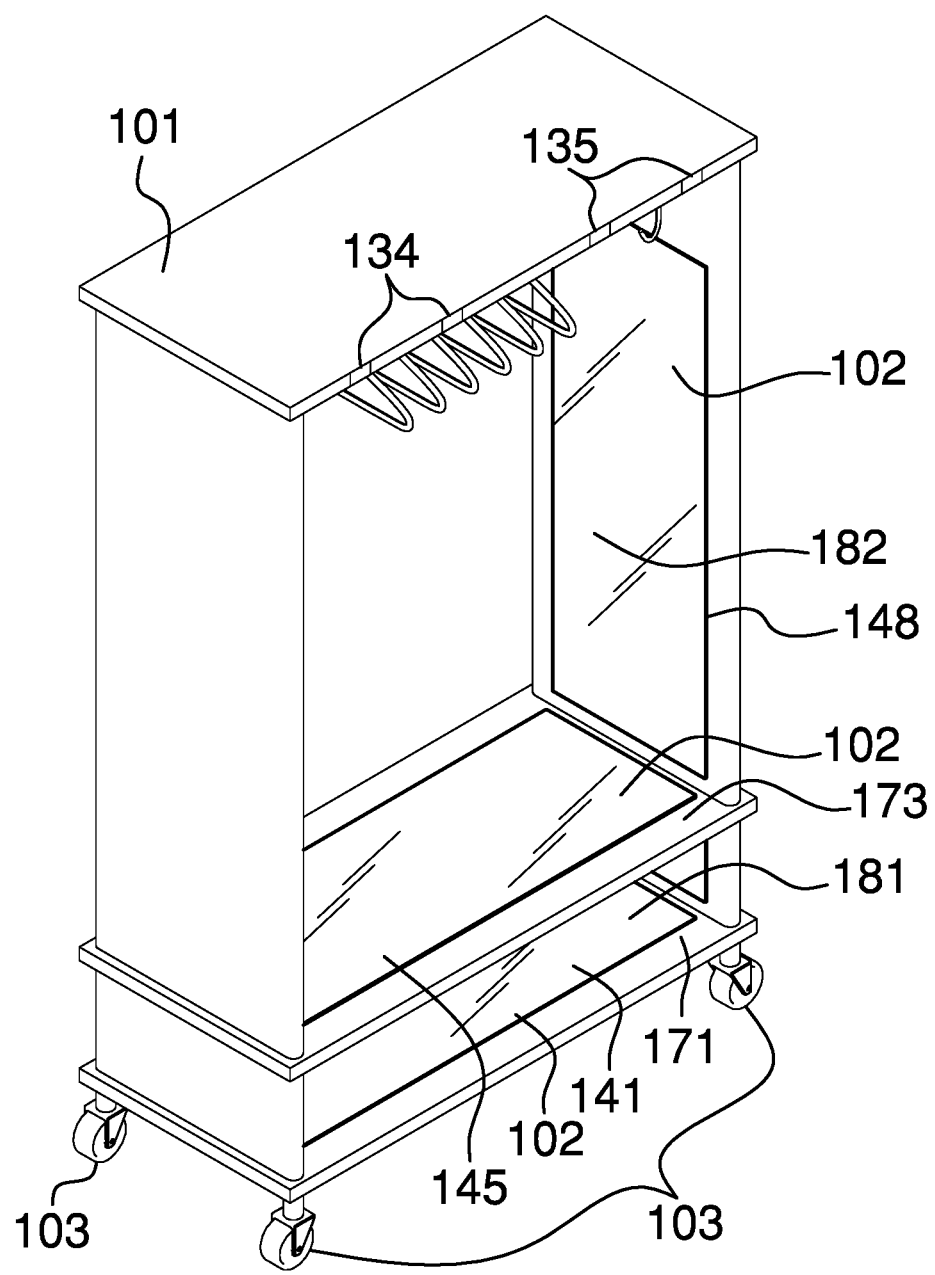
FIG. 1 is a perspective view of an embodiment of the disclosure.
Figure 2:
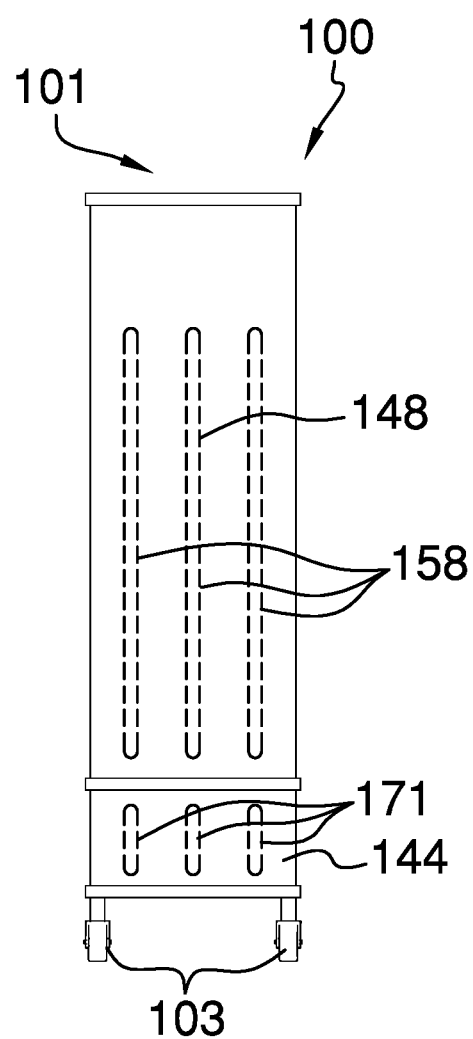
FIG. 2 is a side view of an embodiment of the disclosure.
Figure 3:
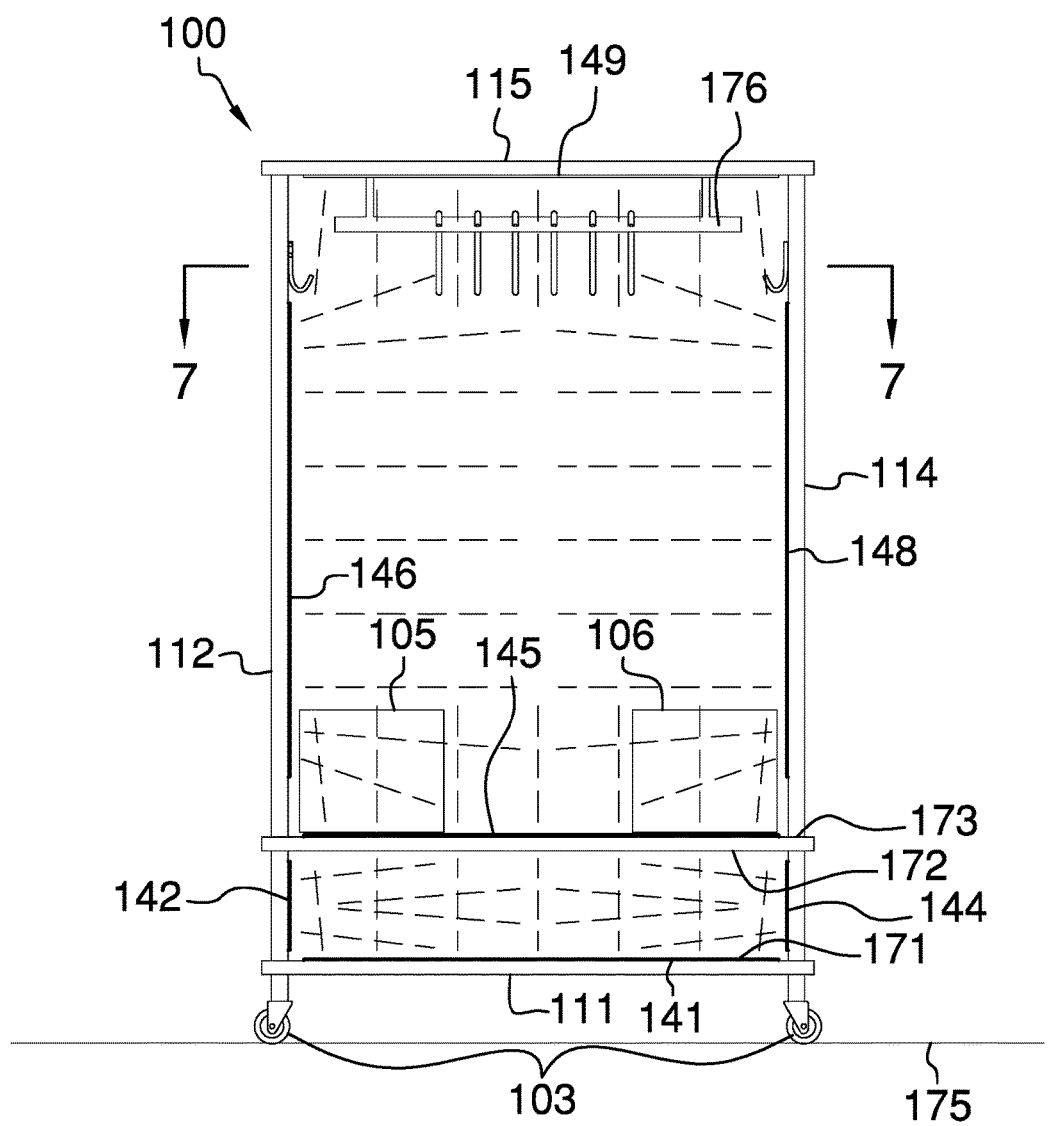
FIG. 3 is a front view of an embodiment of the disclosure.
Figure 4:
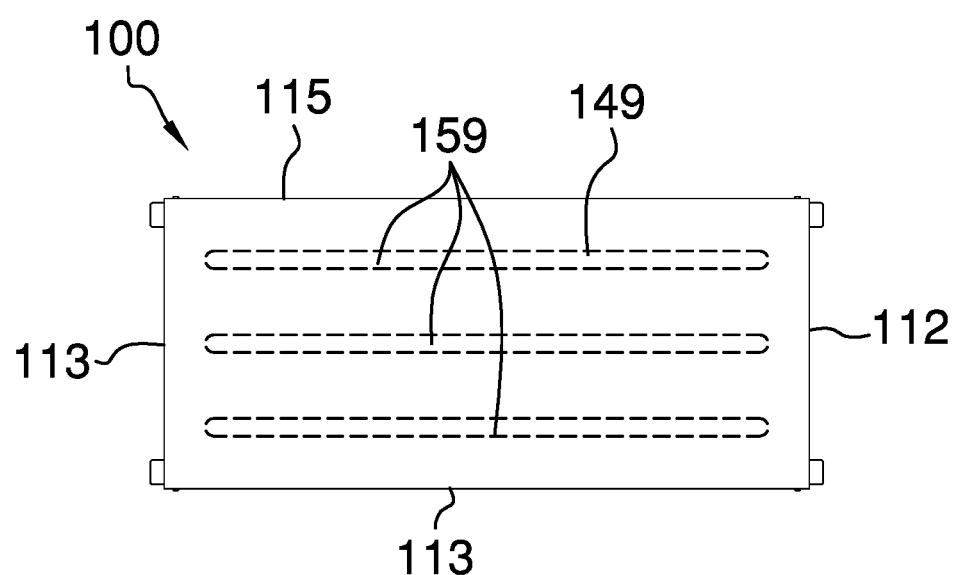
FIG. 4 is a top view of an embodiment of the disclosure.
Figure 5:
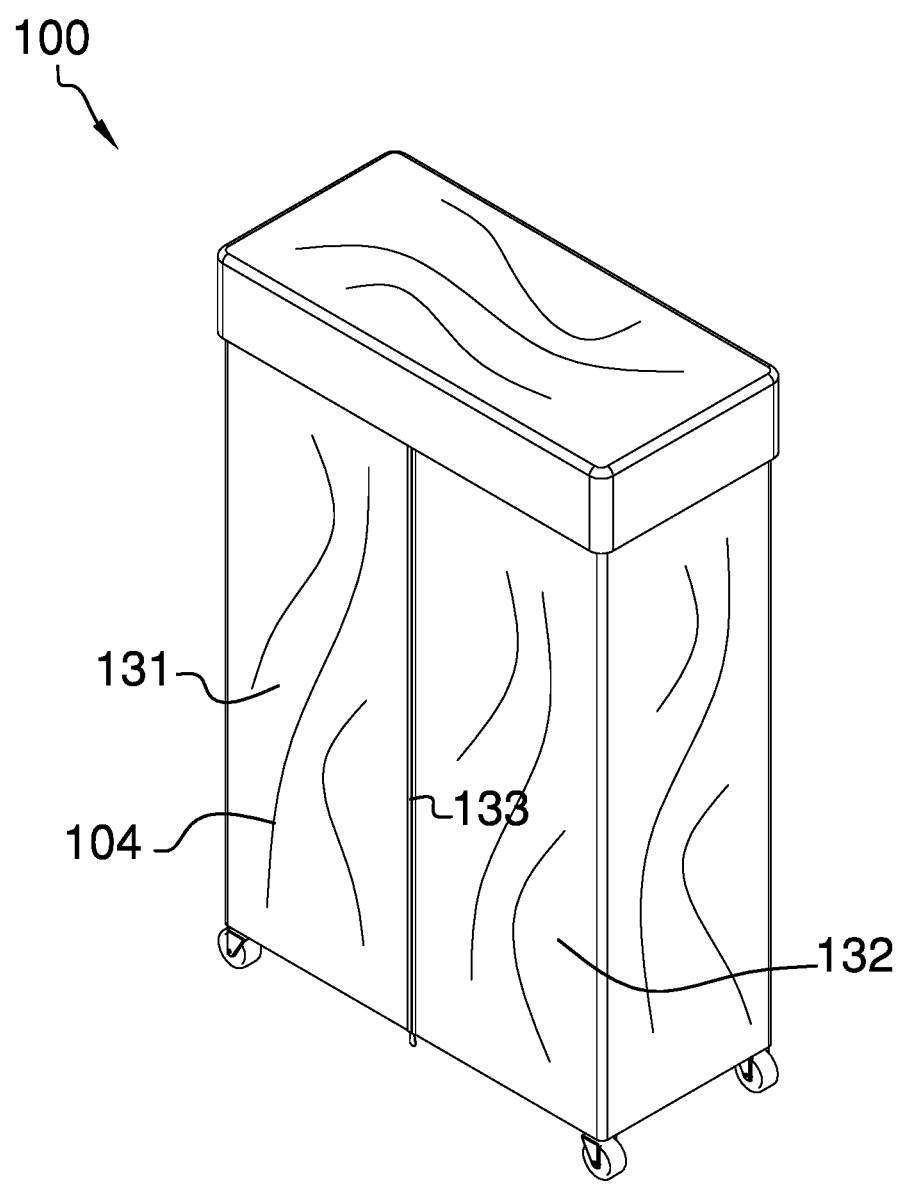
FIG. 5 is a perspective view of an embodiment of the disclosure.
Figure 6:
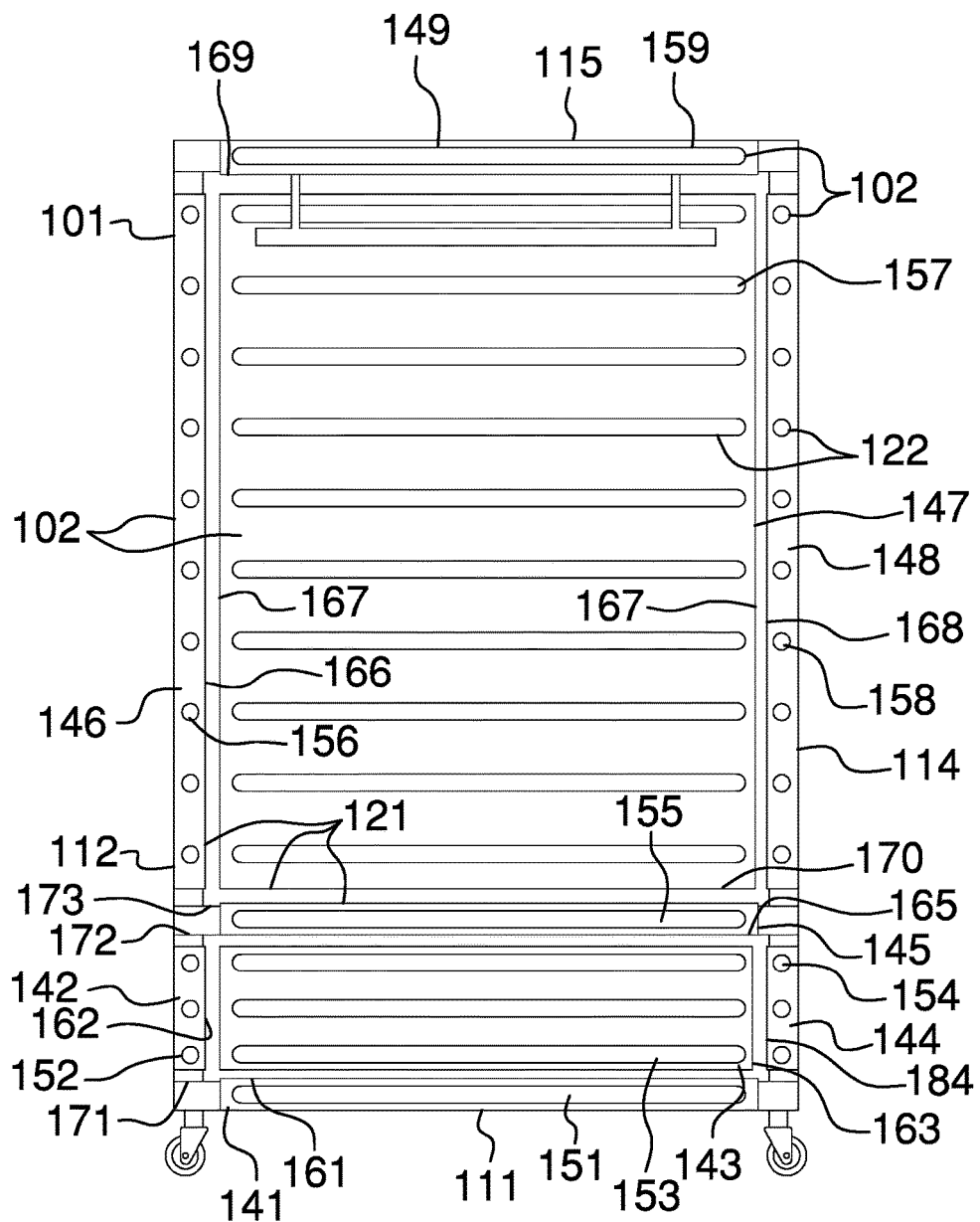
FIG. 6 is detailed front view of an embodiment of the disclosure.
Figure 7:
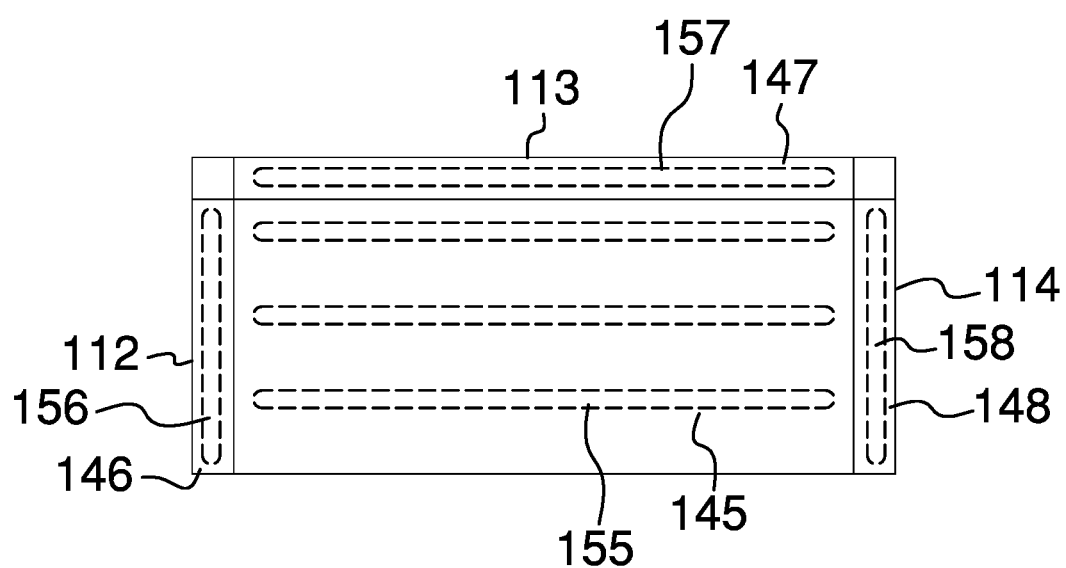
FIG. 7 is a cross-sectional view of an embodiment of the disclosure across 7-7 as shown in FIG. 3.

Detailed reference will now be made to one or more potential embodiments of the disclosure, which are illustrated in FIGS. 1 through 7.

The UV sanitizing device 100 (hereinafter invention) is a wheeled cabinet 101 that is adapted for use in sanitizing the garments, domestic articles, and tools used by health care professionals. The invention 100 uses ultraviolet radiation to sanitize objects contained within the cabinet 101. The interior surfaces of the cabinet 101 supports a plurality of UV chambers 102 that generates the UV radiation required for use in sanitizing the contents of the cabinet 101. The cabinet 101 is further organized into a first chamber 181 and a second chamber 182 such that shoes can be sanitized separately from the other articles being sanitized. The invention 100 comprises a cabinet 101, a plurality of UV chambers 102, a plurality of wheels 103, a closure 104, a first container 105, and a second container 106.

The cabinet 101 is a rectangular block shaped structure that comprises plurality of skins that further comprises a first skin 111, a second skin 112, a third skin 113, a fourth skin 114, and a fifth skin 115. Each of the plurality of skins is a rectangular plate. In the first potential embodiment of the disclosure, each of the plurality of skins is formed from a high density polyethylene. Each of the plurality of skins are assembled into the cabinet 101 such that the cabinet 101 has an open face through which access to the interior of the cabinet 101 is available. In the first potential embodiment of the disclosure, the interior surface of each of the plurality of skins is coated in a mirroring material that reflects UV radiation back into the interior of the cabinet 101 while the invention 100 is in operation. As shown most clearly in FIGS. 6 and 7, the first skin 111, the second skin 112, the fifth skin 115, and the fourth skin 114 forms the basic rectangular structure of the cabinet 101. The third skin 113 encloses the back side of the invention 100. The first skin 111 is proximal to the supporting surface 175 upon which the invention 100 is placed. The fifth skin 115 is the surface of the cabinet 101 that is distal from the first skin 111.

The open face of the cabinet 101 is enclosed by the closure 104. The closure 104 comprises a first textile 131, a second textile 132, a first fastener 133, a second fastener 134, and a third fastener 135. As shown most clearly in FIG. 5, the first textile 131 is a readily and commercially available textile cut in a rectangular shape. The second textile 132 is a readily and commercially available textile cut in a rectangular shape. The second fastener 134 attaches the first textile 131 to the fifth skin 115 such that the first textile 131 drapes from the fifth skin 115 to the first skin 111. The third fastener 135 attaches the second textile 132 to the fifth skin 115 such that the second textile 132 drapes from the fifth skin 115 to the first skin 111. The first fastener 133 attaches the first textile 131 to the second textile 132 such that the closure 104 will enclose the cabinet 101 while the invention 100 is being used. In the first potential embodiment of the disclosure, the first fastener 133 is a readily and commercially available zipper. The second fastener 134 and the third fastener 135 are both readily and commercially available hook and loop fasteners.

Each of the plurality of UV chambers 102 comprises one or more covers 121 and a plurality of UV lamps 122. Each of the plurality of UV lamps 122 comprises the mountings, electrical fixtures, and bulbs necessary to generate the UV radiation used by the invention 100 for sanitizing purposes. It is preferred that that each of the plurality of UV lamps 122 contained within a UV chamber selected from the plurality of UV chambers 102 generate UV radiation in the UV-C range. Ideally, the selected UV lamps would generate UV radiation with a wavelength between 248 nm and 262 nm. Each of the one or more covers 121 is a structure that is transparent to ultraviolet radiation. The cover is a container like structure that forms an enclosed space around the plurality of UV lamps 122 contained within the selected UV chamber. Each of the one or more covers 121 is a guard that effectively separates users from the electrical circuits and the power sources necessary to operate the plurality of UV lamps 122. In the first potential embodiment of the disclosure, each of the one or more covers 121 is molded from a plastic selected from the group consisting of poly(methyl methacrylic) or polycarbonate.

The plurality of UV chambers 102 comprises a first UV chamber 141, a second UV chamber 142, a third UV chamber 143, a fourth UV chamber 144, a fifth UV chamber 145, a sixth UV chamber 146, a seventh UV chamber 147, an eighth UV chamber 148, and a ninth UV chamber 149. The first UV chamber 141 further comprises a first cover 161 and a first plurality of UV lamps 151. The second UV chamber 142 further comprises a second cover 162 and a second plurality of UV lamps 152. The third UV chamber 143 further comprises a third cover 163 and a third plurality of UV lamps 153. The fourth UV chamber 144 further comprises a fourth cover 164, a fourth plurality of UV lamps 154. The fifth UV chamber 145 further comprises a fifth cover 165 and a tenth cover 170, and a fifth plurality of UV lamps 155. The sixth UV chamber 146 further comprises a sixth cover 166 and a sixth plurality of UV lamps 156. The seventh UV chamber 147 further comprises a seventh cover 167 and a seventh plurality of UV lamps 157. The eighth UV chamber 148 further comprises an eighth cover 168 and an eighth plurality of UV lamps 158. The ninth UV chamber 149 further comprises a ninth cover 169 and a ninth plurality of UV lamps 159.

Each of the plurality of wheels 103 is a commercially available caster. Each of the plurality of wheels 103 is mounted on the exterior surface of the first skin 111 such that: 1) the cabinet 101 rests on the plurality of wheels 103 when the invention 100 is placed on the supporting surface 175; and, 2) the invention 100 may be rolled along the supporting surface 175.

The invention 100 is assembled as described in this paragraph and the next paragraph. To assemble the fifth UV chamber 145 the fifth cover 165 attaches to the second skin 112 and the fourth skin 114 such that a second horizontal surface 172 is formed. The fifth plurality of UV lamps 155 are mounted on the second horizontal surface 172 formed by the fourth cover 164 and is enclosed using the tenth cover 170 such that: 1) the fifth plurality of UV lamps 155 are covered; and, 2) a third horizontal surface 173 is formed. The third horizontal surface 173 forms a horizontal surface above the first horizontal surface 171 upon which objects may be placed. The third horizontal surface 173 separates the first chamber 181 from the second chamber 182. The space vertically above the third horizontal surface 173 is the second chamber 182. The space vertically below the second horizontal surface 172 forms usable space within the first chamber 181. The first horizontal surface 171 is discussed further in the next paragraph.

To assemble the first UV chamber 141 the first plurality of UV lamps 151 is mounted on the first skin 111. The first cover 161 then attaches to the first skin 111 such that the first plurality of UV lamps 151 are covered. Once installed, the first cover 161 forms the first horizontal surface 171 of the cabinet 101 upon which shoes and other items may be placed for sanitizing by the UV radiation. To assemble the second UV chamber 142 the second plurality of UV lamps 152 is mounted on the second skin 112. The second cover 162 then attaches to the second skin 112 such that the second plurality of UV lamps 152 are covered. To assemble the third UV chamber 143 the third plurality of UV lamps 153 is mounted on the third skin 113. The third cover 163 then attaches to the third skin 113 such that the third plurality of UV lamps 153 are covered. To assemble the fourth UV chamber 144 the fourth plurality of UV lamps 154 is mounted on the fourth skin 114. The fourth cover 164 then attaches to the fourth skin 114 such that the fourth plurality of UV lamps 154 are covered. To assemble the sixth UV chamber 146 the sixth plurality of UV lamps 156 is mounted on the second skin 112. The sixth cover 166 then attaches to the second skin 112 such that the sixth plurality of UV lamps 156 are covered. To assemble the seventh UV chamber 147 the seventh plurality of UV lamps 157 is mounted on the third skin 113. The seventh cover 167 then attaches to the third skin 113 such that the seventh plurality of UV lamps 157 are covered. To assemble the eighth UV chamber 148 the eighth plurality of UV lamps 158 is mounted on the fourth skin 114. The eighth cover 168 then attaches to the fourth skin 114 such that the eighth plurality of UV lamps 158 are covered. To assemble the ninth UV chamber 149 the ninth plurality of UV lamps 159 is mounted on the fifth skin 115. The ninth cover 169 then attaches to the fifth skin 115 such that the ninth plurality of UV lamps 159 is covered.

Methods to make the attachments as described in the prior two paragraphs are well known and documented in the electrical and mechanical arts.

The invention 100 is finished in the following manner. A first container 105 and a second container 106 formed from a material that is transparent to UV radiation are placed on the third horizontal surface 173. The purpose of the first container 105 and the second container 106 is to contain domestic articles and tools that are used by medical personnel. A clothes bar 176 mounts between the sixth cover 166 and the eighth cover 168 such that garments may be hung within the cabinet 101.

To use the invention 100, the items to be sanitized are placed within the cabinet 101. Power is then applied to the plurality of UV chambers 102 such that the plurality of UV lamps 122 generates UV radiation.

The following definitions were used in this disclosure:

Caster: As used in this disclosure, a caster is a wheel that is mounted on a swivel that allows the wheel to adjust, or swivel, the direction of rotation of the wheel to the direction of motion desired for the wheel.

Domestic Article: As used in this disclosure, a domestic article is an item or object: 1) that is commonly found within a household; or, 2) that is commonly carried by a person. Examples of domestic articles include, but are not limited to, keys and key fobs, personal data devices, glasses, remote controls, or personal storage items such as purses, briefcases, wallets, or cases.

Exterior: As used in this disclosure, the exterior is use as a relational term that implies that an object is not contained within the boundary of a structure or a space.

Fastener: As used in this disclosure, a fastener is a device that is used to join or affix two objects. Fasteners generally comprise a first element, which is attached to the first object and a second element which is attached to the second object such that the first element and the second element join to affix the first object and the second object.

Hook and Loop Fastener: As used in this disclosure, a hook and loop fastener is a fastener that comprises a hook surface and a loop surface. The hook surface comprises a plurality of minute hooks. The loop surface comprises a surface of uncut pile that acts like a plurality of loops. When the hook surface is applied to the loop surface, the plurality of minute hooks fastens to the plurality of loops securely fastening the hook surface to the loop surface. A note on usage: when fastening two objects the hook surface of a hook and loop fastener will be placed on the first object and the matching loop surface of a hook and loop fastener will be placed on the second object without significant regard to which object of the two objects is the first object and which of the two objects is the second object. When the hook surface of a hook and loop fastener or the loop surface of a hook and loop fastener is attached to an object this will simply be referred to as the "hook or loop surface" with the understanding that when the two objects are fastened together one of the two objects will have a hook surface and the remaining object will have the loop surface.

Horizontal: As used in this disclosure, horizontal is a directional term that refers to a direction that is either: 1) parallel to the horizon; 2) perpendicular to the local force of gravity, or, 3) parallel to a supporting surface 175. In cases where the appropriate definition or definitions are not obvious, the second option should be used in interpreting the specification. Unless specifically noted in this disclosure, the horizontal direction is always perpendicular to the vertical direction.

Interior: As used in this disclosure, the interior is use as a relational term that implies that an object is contained within the boundary of a structure or a space.

Textile: As used in this disclosure, a textile is a material that is woven, knitted, braided or felted. Synonyms in common usage for this definition include fabric and cloth.

Ultraviolet Light: As used in this disclosure, ultraviolet light is understood to be electromagnetic radiation with a wavelength lesser than visible light. In general usage, ultraviolet light is taken to mean electromagnetic radiation with a wavelength less than 400 nm.

Ultraviolet C Light: As used in this disclosure, ultraviolet C light is understood to be ultraviolet light with wavelengths in the range of 200 nm to 300 nm. Ultraviolet C light is considered to be the most effective light for disinfection. Within the ultraviolet C range, the most effective disinfection is considered to occur with radiation wavelengths between 248 nm and 262 nm.

UV: As used in this disclosure, UV is an abbreviation for ultraviolet.

Vertical: As used in this disclosure, vertical refers to a direction that is either: 1) perpendicular to the horizontal direction; 2) parallel to the local force of gravity; or, 3) when referring to an individual object the direction from the designated top of the individual object to the designated bottom of the individual object. In cases where the appropriate definition or definitions are not obvious, the second option should be used in interpreting the specification. Unless specifically noted in this disclosure, the vertical direction is always perpendicular to the horizontal direction.

Zipper: As used in this disclosure, a zipper is a fastening device comprising two flexible strips with interlocking components that are opened and closed by pulling a slide along the two flexible strips.

With respect to the above description, it is to be realized that the optimum dimensional relationship for the various components of the invention described above and in FIGS. 1 through 7 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An apparatus comprising:
  wherein the apparatus comprises a cabinet, a plurality of UV chambers, a plurality of wheels, a closure, a first container, and a second container;
  the plurality of UV chambers mount on the interior surfaces of the cabinet;
  the first container and the second container are placed within the interior of the cabinet;
  the closure and the plurality of wheels are mounted on the exterior of the cabinet;
  wherein the apparatus is a mobile cabinet that is adapted to sanitize contents of the cabinet via the UV chambers;
  wherein the apparatus comprises a plurality of UV lamps that uses ultraviolet radiation to sanitize objects contained within the cabinet;
  wherein the cabinet is further organized into a first chamber and a second chamber;
  wherein the cabinet is a block shaped structure;
  wherein the cabinet comprises a plurality of skins;

wherein the plurality of skins further comprises a first skin, a second skin, a third skin, a fourth skin, and a fifth skin;
wherein each of the plurality of skins is a rectangular plate;
wherein the plurality of skins are assembled into the cabinet such that the cabinet has an open face;
the first skin, the second skin, the fifth skin, and the fourth skin forms the block shaped structure of the cabinet;
the third skin encloses the back side of the apparatus;
the first skin is proximal to a supporting surface upon which the apparatus is placed;
the fifth skin is the surface of the cabinet that is distal from the first skin;
the open face of the cabinet is enclosed by the closure;
wherein the closure comprises a first textile, a second textile, a first fastener, a second fastener, and a third fastener;
wherein the first textile is a textile cut in a rectangular shape;
wherein the second textile is a textile cut in a rectangular shape;
the second fastener attaches the first textile to the fifth skin such that the first textile drapes from the fifth skin to the first skin;
the third fastener attaches the second textile to the fifth skin such that the second textile drapes from the fifth skin to the first skin;
the first fastener attaches the first textile to the second textile such that the closure encloses the cabinet when in use;
each of the plurality of UV chambers comprises one or more covers and one of the plurality of UV lamps;
each of the plurality of UV lamps generate the UV radiation;
each cover selected from the one or more covers is a structure that is transparent to ultraviolet radiation;
wherein the selected cover is a container that forms an enclosed space around the associated plurality of UV lamps;
wherein the plurality of UV chambers comprises a first UV chamber, a second UV chamber, a third UV chamber, a fourth UV chamber, a fifth UV chamber, a sixth UV chamber, a seventh UV chamber, an eighth UV chamber, and a ninth UV chamber;
wherein the first UV chamber further comprises a first cover and a first UV lamp of the plurality of UV lamps;
wherein the second UV chamber further comprises a second cover and a second UV lamp of the plurality of UV lamps;
wherein the third UV chamber further comprises a third cover and a third UV lamp of the plurality of UV lamps;
wherein the fourth UV chamber further comprises a fourth cover, a fourth UV lamp of the plurality of UV lamps;
wherein the fifth UV chamber further comprises a fifth cover and a tenth cover, and a fifth UV lamp of the plurality of UV lamps;
wherein the sixth UV chamber further comprises a sixth cover and a sixth UV lamp of the plurality of UV lamps;
wherein the seventh UV chamber further comprises a seventh cover and a seventh UV lamp of the plurality of UV lamps;
wherein the eighth UV chamber further comprises an eighth cover and an eighth UV lamp of the plurality of UV lamps;
wherein the ninth UV chamber further comprises a ninth cover and a ninth UV lamp of the plurality of UV lamps;
wherein the fifth UV chamber the fifth cover attaches to the second skin and the fourth skin such that a second horizontal surface is formed;
the fifth UV lamp of the plurality of UV lamps are mounted on the second horizontal surface formed by the fourth cover;
the fifth UV lamp of the plurality of UV lamps are enclosed using the tenth cover such that the fifth plurality of UV lamps are covered;
wherein the fifth UV lamp of the plurality of UV lamps are enclosed using the tenth cover such that the fifth UV lamp of the plurality of UV lamps are covered such that a third horizontal surface is formed;
wherein the third horizontal surface forms a horizontal surface above the first horizontal surface upon which objects may be placed;
the third horizontal surface separates the first chamber from the second chamber;
the space vertically above the third horizontal surface is the second chamber;
the space vertically below the second horizontal surface forms the first chamber;
the first UV lamp of the plurality of UV lamps is mounted on the first skin;
the first cover attaches to the first skin such that the first UV lamp of the plurality of UV lamps are covered;
the first cover forms the first horizontal surface of the cabinet;
the second UV lamp of the plurality of UV lamps is mounted on the second skin;
the second cover attaches to the second skin such that the second UV lamp of the plurality of UV lamps are covered;
the third UV lamp of the plurality of UV lamps is mounted on the third skin;
the third cover attaches to the third skin such that the third UV lamp of the plurality of UV lamps are covered;
the fourth UV lamp of the plurality of UV lamps is mounted on the fourth skin;
the fourth cover attaches to the fourth skin such that the fourth UV lamp of the plurality of UV lamps are covered;
the sixth UV chamber the sixth UV lamp of the plurality of UV lamps is mounted on the second skin;
the sixth cover attaches to the second skin such that the sixth UV lamp of the plurality of UV lamps are covered;
the seventh UV chamber the seventh UV lamp of the plurality of UV lamps is mounted on the third skin;
the seventh cover attaches to the third skin such that the seventh UV lamp of the plurality of UV lamps are covered;
the eighth UV chamber the eighth UV lamp of the plurality of UV lamps is mounted on the fourth skin;
the eighth cover attaches to the fourth skin such that the eighth UV lamp of the plurality of UV lamps are covered;
the ninth UV lamp of the plurality of UV lamps is mounted on the fifth skin;
the ninth cover attaches to the fifth skin such that the ninth UV lamp of the plurality of UV lamps are covered;
wherein the first container is a first storage container that is formed from a material that is transparent to UV radiation;

wherein a second container is a second storage container is formed from a material that is transparent to UV radiation;
wherein the interior surface of each of the plurality of skins is coated in a mirroring material that reflects UV radiation;
each of the plurality of UV lamps generate UV radiation in the UV-C range;
each of the plurality of wheels is mounted on the exterior surface of the first skin such that the cabinet rests on the plurality of wheels when the apparatus is placed on the supporting surface;
each of the plurality of wheels is mounted on the exterior surface of the first skin such that the apparatus may be rolled along the supporting surface;
wherein each of the plurality of wheels is a caster;
wherein the first fastener is a zipper;
wherein the second fastener is a first hook and loop fastener;
wherein the third fastener is a second hook and loop fastener;
wherein a clothes bar mounts between the sixth cover and the eighth cover;
wherein each of the plurality of UV lamps generate UV radiation with a wavelength between 248 nm and 262 nm;
each of the one or more covers is molded from a plastic selected from the group consisting of poly(methyl methacrylic) or polycarbonate;
wherein each of the plurality of skins is formed from a high density polyethylene.

2. The apparatus according to claim 1 wherein the interior surface of each of the plurality of skins is coated in a mirroring material that reflects UV radiation.

3. The apparatus according to claim 2
each of the plurality of wheels is mounted on the exterior surface of the first skin such that the cabinet rests on the plurality of wheels when the apparatus is placed on the supporting surface;
each of the plurality of wheels is mounted on the exterior surface of the first skin such that the apparatus may be rolled along the supporting surface;
wherein each of the plurality of wheels is a caster.

* * * * *